United States Patent [19]

Bourbon et al.

[11] Patent Number: 5,681,753

[45] Date of Patent: Oct. 28, 1997

[54] SOLUTION CONTAINING A NITROXIDE RADICAL FOR MAGNETOMETRY BY NUCLEAR MAGNETIC RESONANCE

[75] Inventors: Carole Bourbon, La Buisse; Mehdi Moussavi, Meylan, both of France

[73] Assignee: Commissariat a l'Energie Atomique, Paris, France

[21] Appl. No.: 568,757

[22] Filed: Dec. 7, 1995

[30] Foreign Application Priority Data

Dec. 7, 1994 [FR] France ................... 94 14705

[51] Int. Cl.$^6$ .............................. G01N 24/00; G01V 3/00
[52] U.S. Cl. ........................ 436/173; 324/301; 324/303
[58] Field of Search .......................... 436/173; 324/301, 324/303; 548/470, 475

[56] References Cited

U.S. PATENT DOCUMENTS

| | | | |
|---|---|---|---|
| 3,249,856 | 5/1966 | LeMaire et al. | 324/301 |
| 3,495,163 | 2/1970 | Salvi | 324/301 |
| 3,642,818 | 2/1972 | Rassat et al. | 436/173 X |
| 3,702,831 | 11/1972 | Chiarelli et al. | 436/173 X |
| 3,735,246 | 5/1973 | Glenat et al. | 324/301 |
| 3,966,409 | 6/1976 | Hrvoic et al. | 436/173 |

FOREIGN PATENT DOCUMENTS

| | | |
|---|---|---|
| 1268464 | 5/1990 | Canada . |
| 0 423 033 A1 | 4/1991 | European Pat. Off. . |
| 1447226 | 6/1966 | France . |

OTHER PUBLICATIONS

Y. Motozato et al. *Can. J. Chem.* 1982, 60, 1959–1961.
P.G. Griffiths et al. *Aust. J. Chem.* 1983, 36, 397–401.
N. Kerneuez et al. *IEEE Trans, Magnet.* 1992, 28, 3054–3059.
D.G. Gillies et al. *J. Chem. Soc. Faraday Trans.* 1994, 90, 2345–2349.
Bolton, et al., "An EPR and NMR Study of some Tetramethylisoindolin-2-yloxyl Free Radicals," *Journal of the Chemical Society*, Perkin Transactions 2 –pp. 2049–2052 (1993).

Primary Examiner—Arlen Soderquist
Attorney, Agent, or Firm—Burns, Doane, Swecker & Mathis LLP

[57] ABSTRACT

The invention relates to a solution containing a nitroxide radical for magnetometry by nuclear magnetic resonance. This solution is constituted by a nitroxide radical of formula:

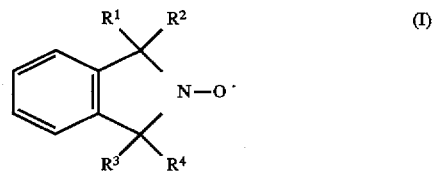

in which $R^1$, $R^2$, $R^3$ and $R^4$, which can be the same or different, represent an alkyl group or an alkoxy group which may be deuterated, or in which the pairs $R^1$–$R^2$ and/or $R^3$–$R^4$ together form an optionally deuterated cycloalkyl or polycycloalkyl group, and N represent $^{14}N$ or $^{15}N$, dissolved in a solvent having an oxidizing power and an appropriate viscosity.

The solvent can be constituted by a mixture of water and two compounds respectively playing the part of the oxidizing agent and viscosity modifying agent, e.g. water, ethylene glycol and $NaIO_4$, or can be solely constituted by a mixture of water and an oxidizing agent able to modify the viscosity, such as acetic acid.

11 Claims, 2 Drawing Sheets

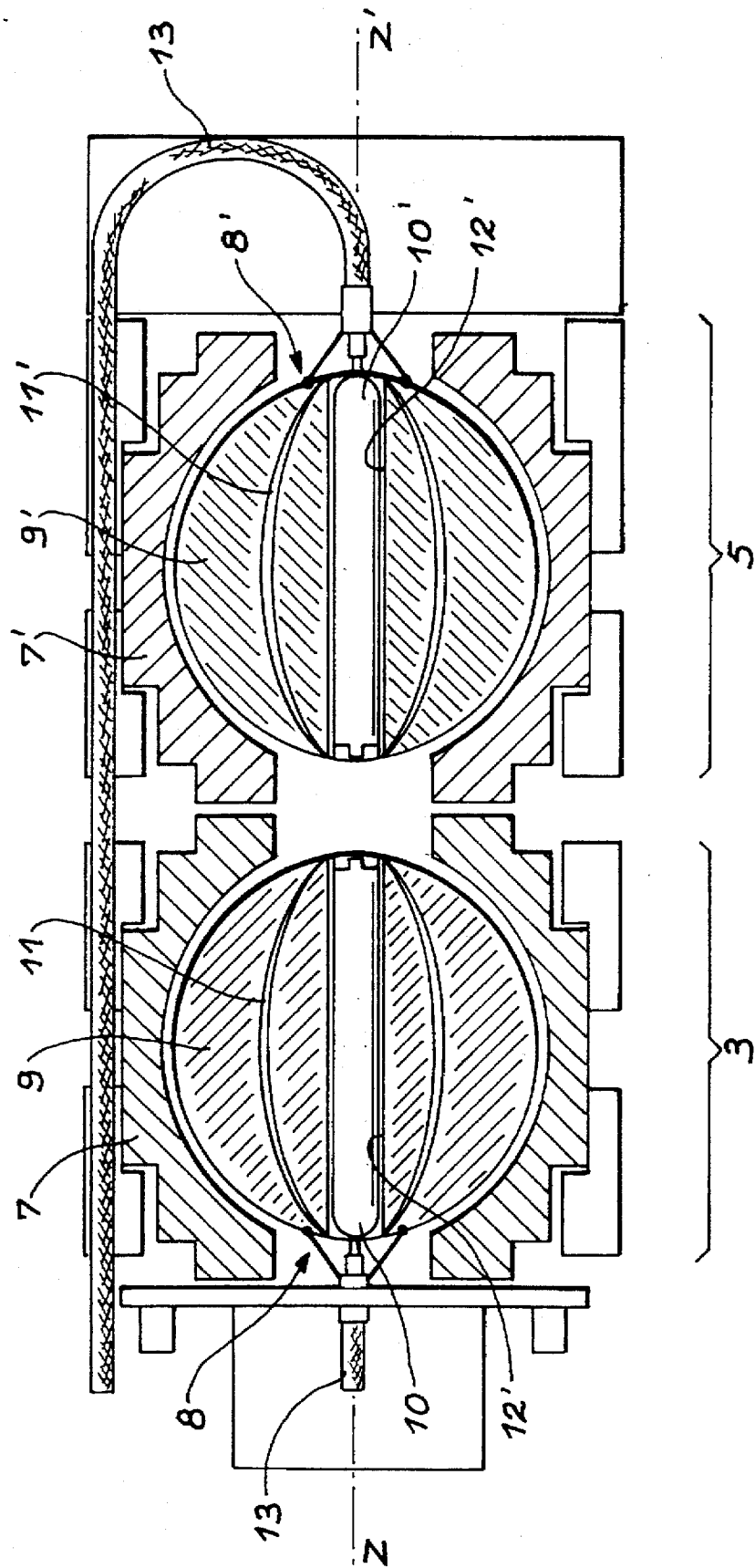

SOLUTION CONTAINING A NITROXIDE RADICAL FOR MAGNETOMETRY BY NUCLEAR MAGNETIC RESONANCE

BACKGROUND OF THE INVENTION

The present invention relates to a nitroxide radical solution in a solvent usable in magnetometry by nuclear magnetic resonance (NMR).

It more particularly relates to magnetometry in a weak magnetic field using NMR methods with dynamic polarization of the nuclei of a solvent.

It is known that in terrestrial field magnetometers using magnetic resonance of nuclei, the main problem is that of the polarization, i.e. the forced orientation of the spins, or the kinetic moments of the nuclei, particularly protons of the solvent in which the radical is dissolved in an appropriate proportion.

According to FR-A-1 174 136, this polarization can be obtained by the coupling of the unpaired electron of a free radical, whose electron paramagnetic resonance line is saturated by an appropriate, high frequency field, with the nuclei of the solvent.

Magnetometers using nuclear magnetic resonance operating on the basis of this principle and such as are described in FR-A-1 447 226 and FR-A-2 098 624, are very high performance magnetometers for the measurement of weak magnetic fields.

As they are isotropes, i.e. they make it possible to directly know the value of the modulus of the magnetic field, independently of the direction of the sensor with respect to that of the vector which they measure, they can have applications in numerous fields requiring a high sensitivity such as:

seeking cracks in the ocean and pipelines, magnetic cartography on archeological sites, the monitoring of volcanos, magnetic stratigraphy in drilled or bored wells and the military sector.

These magnetometers with spin coupling nuclear magnetic resonance generally have a head or sensor in which coils are associated with at least one material sample having a gyromagnetic property and are connected to the input and output of a linear amplifier for forming a loop, in which the nuclear oscillation frequency is measured.

The material sample having a gyromagnetic property is constituted by a paramagnetic substance such as a free radical having an unpaired electron dissolved in a solvent having atomic nuclei with non-zero kinetic moment and magnetic moment. Usable solvents are e.g. alcohols and ethers such as methanol, octanol, ethylene glycol and dimethoxy ethane.

Usable free radicals are e.g. described in EP-A-185 825, FR-A-2 063 416 and U.S. Pat. No. 3,966,409. Among these, particular use is made of the compounds of EP-A-185 825 complying with the following formulas:

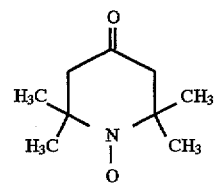

2,2,6,6-tetramethly-4-piperidinone-1-oxyl, hereinafter called "TANO"

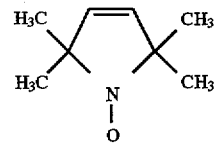

2,2,5,5-tetramethly-4-pyrroline-1,oxyl, hereinafter called "TANANE"

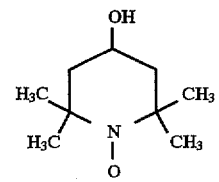

2,2,6,6-tetramethly piperidinol-1-oxyl, hereinafter called "TANOL"

in which the hydrogen atoms can be wholly or partly replaced by deuterium atoms and the nitrogen can be nitrogen 14 or nitrogen 15.

Hitherto, the best results for magnetometry have been obtained with the radicals TANO 15D, i.e. the aforementioned TANO completely deuterated with $^{15}N$, and TANANE 15, i.e. the aforementioned TANANE deuterated with $^{15}N$.

However, these free radicals are not completely suitable in the field of oil prospecting, which require the sensors to have an optimum operation at ever higher temperatures. Thus, with a mean geothermal gradient of 2° C./100 m, the well bottom temperatures can reach 150° or even 200° C., as a function of the nature of the soil or ground and the proximity of hot sources, and the aforementioned nitroxide radicals are unable to withstand these temperatures, because they have a limited life beyond 70° C.

Thus, in the protonated medium, under the effect of heat, TANANE transforms in the following way:

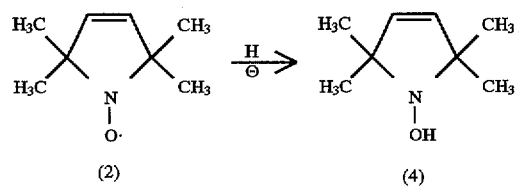

At the high temperatures reached at the bottom of wells, there is consequently a progressive and irreversible disappearance of the nitroxide radical, which is converted into hydroxylamine.

3

Thus, at 150° C., a TANANE solution in a concentration of $10^{-3}$ mole/l in water containing 5% 2-methoxyethyl ether loses 20% of the signal after 40 hours at this temperature and 50% after 300 hours at this temperature. At 180° C. the disappearance of the radical is even more significant: 20% of the signal at least after 20 hours at this temperature and 50% after 50 hours at said temperature.

Therefore for measurement in wells for several hours where the probes becomes unusable after 20 to 30 hours at 180° C. no longer have any interest.

EP-A-423 033 proposes the use of nitroxide radicals and solvents having a better hot stability than TANANE, but this stability does not exceed a temperature of 130° C., which is inadequate, as has been shown hereinbefore.

SUMMARY OF THE INVENTION

The present invention is directed at a solution containing a nitroxide radical, which is usable for magnetometry by nuclear magnetic resonance at temperatures which can reach 200° C. and for long periods.

According to the invention, the solution containing a nitroxide radical is characterized in that it is constituted by a nitroxide radical of formula:

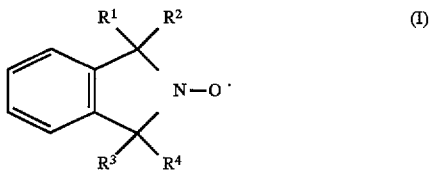

(I)

in which $R^1$, $R^2$, $R^3$ and $R^4$, which can be the same or different, represent an optionally deuterated alkoxy or alkyl group, or in which the $R^1$-$R^2$ and/or $R^3$-$R^4$ pairs together form an optionally deuterated cycloalkyl or polycycloalkyl group, and N represents $^{14}$N or $^{15}$N, dissolved in a solvent constituted by a mixture of water and at least one compound, the compound or compounds being chosen in such a way that the solution contains an oxidizing agent of the reduced form of the nitroxide radical and has an appropriate viscosity for magnetometry at temperatures from 20° to 200° C.

DETAILED DESCRIPTION OF THE INVENTION

According to the invention, the $R^1$, $R^2$, $R^3$ and $R^4$ groups can be alkyl or alkoxy groups or can together form cycloalkyl or polycycloalkyl groups. The alkyl or alkoxy groups which can be used can be straight or branched groups, generally having 1 to 5 carbon atoms, whereof all or part of the hydrogen atoms can be replaced by deuterium atoms (D).

When $R^1$-$R^2$ and/or $R^3$-$R^4$ together form a cycloalkyl group, the latter preferably has 4 to 11 carbon atoms. When these groups form together a polycycloalkyl group, they can be adamantyl radicals. Preferably $R^1$, $R^2$, $R^3$ and $R^4$ are lower alkyl groups with 1 to 4 carbon atoms and in particular methyl groups.

In this nitroxide radical, the nitrogen atom can be $^{14}$N or $^{15}$N. Preference is given to $^{15}$N. Preference is also given to the use of deuterated alkyl or alkoxy groups for $R^1$, $R^2$, $R^3$ and $R^4$.

As examples of appropriate nitroxide radicals, reference can be made to those complying with the formulas:

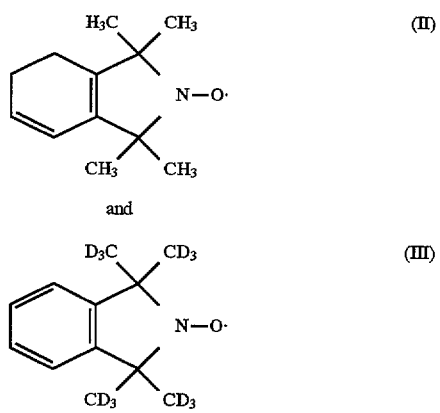

According to the invention, the use of a nitroxide radical complying with the above formulas II and III makes it possible to obtain an improved stability of the solution compared with what is obtained with the TANANE-type radical.

Thus, the addition to the nitroxide radical of the 2,2,5,5-tetramethylpyrrolidine-1-oxyl type of a cycle having 6 carbon atoms, formed by a benzene cycle, makes it possible to increase the volume of the molecule, rigidify it so as to form therefrom a planar molecule and increase its stability. Thus, dissolved in water at a concentration of $10^{-3}$ mole/l, the nitroxide radical of formula

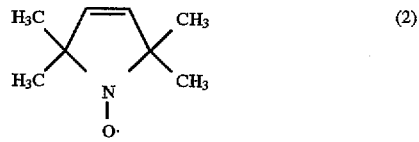

(2)

has a half-life of 250 hours at 150° C., whilst the nitroxide radical of formula II used in the invention at the same temperature has a half-life greatly exceeding 250 hours, because the signal loss is only 10% at the end of 300 hours.

It is pointed that the half-life of a nitroxide radical corresponds to the time which has elapsed between the instant at which the radical is raised to the desired temperature and the instant at which the EPR signal of said radical has lost 50% of its initial value.

According to the invention, the solvent used in the solution plays an important part, because it makes it possible on the one hand to have an appropriate viscosity at the measurement temperature in the magnetometer and on the other stabilizes the nitroxide radical avoiding its conversion into hydroxylamine as a result of the presence of an oxidizing agent.

In order to obtain this result, the solvent is constituted by water to which is added one or more compounds able to fulfil these different functions.

According to a first embodiment of the invention, to the water are added two compounds, whereof one is an oxidizing agent and the other an organic compound compatible with the nitroxide radical and having a viscosity higher than that of water. This organic compound can be chosen from among alcohols, polyalcohols and ethers and in particular those already used for the manufacture of NMR probes of magnetometers.

According to the invention, the organic compound is preferably ethylene glycol and it is preferably used in a quantity so that it represents 20 to 30 vol. % of the solvent.

In the water-ethylene glycol mixture, the water has a destabilizing action by disorganizing the bonds between the ethylene glycol molecules, which makes the hydrogen atoms much more exposed and therefore much more reactive with the nitroxide radical. It is therefore possible to accelerate the disappearance process of this radical in accordance with the following reaction diagram:

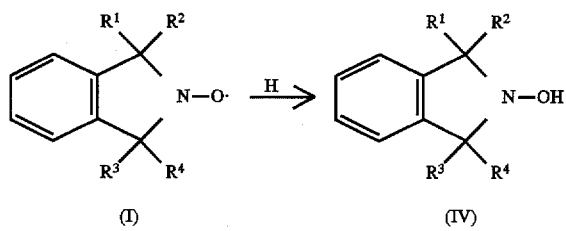

According to the invention, this situation is remedied by the fact that the solution also contains an oxidizing agent in order to bring about the in situ regeneration of the nitroxide radical according to the following reaction diagram:

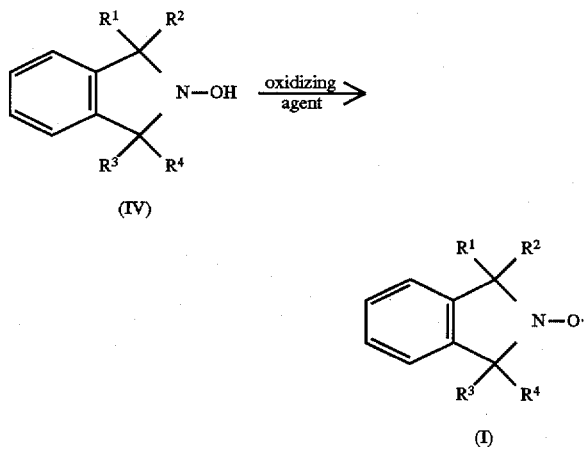

The oxidizing agents which can be used for this purpose can be of different types, but agents which are too reactive at high temperatures must be avoided, because the volume cannot be expanded in a magnetometer probe.

In addition, the known oxidizing agents used for the preparation of nitroxide radicals from hydroxylamine such as $WO_5^{—}$, $CH_3CN/H_2O_2$ and m-chloroperbenzoic acid are not suitable because they are too reactive.

As examples, it is possible to use less reactive oxidizing agents chosen from among metaperiodates of alkali metals such as $KIO_4$ and $NaIO_4$, and lead dioxide $PbO_2$.

In general, the solution contains $10^{-2}$ to $5.10^{-1}$ mole/l of oxidizing agent.

According to a second preferred embodiment of the invention, to the water partly forming the solvent is added a single compound able to fulfil the two functions, i.e. an oxidizing agent having a viscosity higher than that of water. Reference is made to acetic acid as an example of such a compound. When acetic acid is used, it can represent 20 to 50 vol. % of the solvent.

In the nitroxide radical solution of the invention, the nitroxide radical concentration is chosen in such a way as to obtain good results in magnetometry. Generally this concentration is in the range $10^{-3}$ to $10^{-2}$ mole/l.

The nitroxide radicals of formula (I) used in the invention can be prepared by conventional processes. It is in particular possible to use the synthesis method described in Aust. J. Chem., 1983, 36, pp 397–401.

The invention also relates to a nuclear magnetic resonance magnetometer probe, without forbidden axis and having two assemblies, each constituted by a coil surrounding a container filled with a sample constituted by a solution containing a nitroxide radical, and two resonant cavities for exciting the two samples to two different frequencies, characterized in that the samples are a solution of a nitroxide radical according to the invention.

BRIEF DESCRIPTION OF THE DRAWINGS

Other features and advantages of the invention can be better gathered from the following description given in a non-limitative, illustrative manner with reference to the attached drawings, wherein show:

FIG. 3 Diagrammatically a nuclear magnetic resonance probe according to the invention.

The following examples illustrate two embodiments of a solution containing a nitroxide radical according to the invention. In these two examples, use is made as the nitroxide radical of the radical of formula (III), in which N is $^{15}N$. This nitroxide radical is obtained by following the operating procedure described in Aust. J. Chem., 1983, 36, pp 397–401, using completely deuterated methyl magnesium iodide.

EXAMPLE 1

In this example, which corresponds to the first embodiment of the invention, the solvent is constituted by a mixture of water and ethylene glycol containing 75 vol. % water and 25 vol. ethylene glycol and in said solution are dissolved $10^{-3}$ mole/l of the nitroxide radical of formula (III) and 10.6 g/l ($5.10^{-2}$ mole/l) of $NaIO_4$.

This solution is raised to a temperature of 180° C. for several days, i.e. under conditions where the nitroxide radical should be destroyed and then determination takes place on an electron paramagnetic resonance spectrometer (EFR) at 280 MHz of the spectrum of the nitroxide radical. The spectrum obtained is shown in FIG. 1 (spectrum 1).

Figure 1:
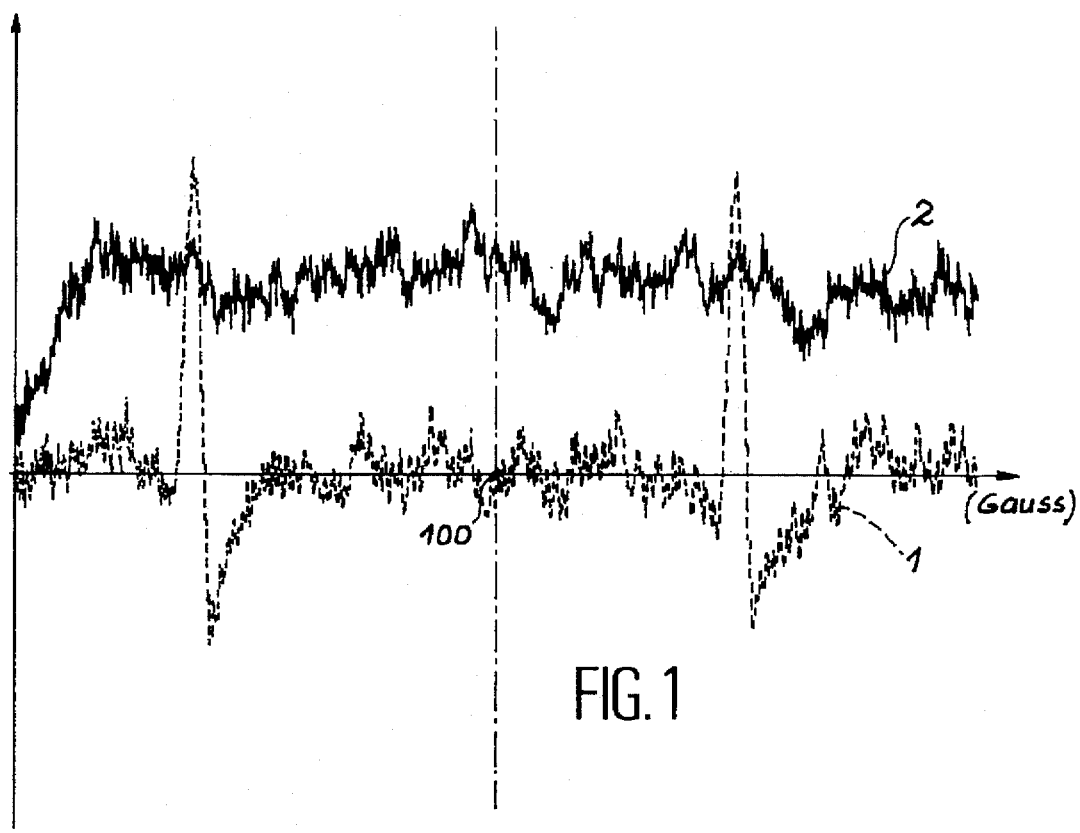
FIG. 1 The electron paramagnetic resonance spectra of a nitroxide radical used in the invention, after several days at 180° C. and in the presence of an oxidizing agent constituted by $NaIO_4$ (spectrum 1) and without oxidizing agent (spectrum 2).

FIG. 1 also shows the spectrum of the same solution, taken under the same conditions (180° C.), but without the addition of the oxidizing agent $NaIO_4$ (spectrum 2).

When these two spectra are compared, it can be seen that only spectrum 1 has the two lines of the nitroxide radical. Spectrum 2 shows a complete destruction of the signal due to the nitroxide radical.

Thus, after spending several days at 180° C., the solution should no longer contain the nitroxide radical, but according to the invention, the presence of an oxidizing agent prevents the deterioration of the nitroxide radical.

EXAMPLE 2

In this example, which corresponds to the second embodiment of the invention, preparation takes place of a solution of the nitroxide radical of formula (III) at a concentration of $10^{-3}$ mole/l in a mixture of water and acetic acid containing 50 vol. % of acetic acid. The properties of this solution are determined on an EPR spectrometer at 9 GHz, raising the solution to 150° C. and periodically determining the spectrum. Following the determination of each spectrum, an estimate is made of the nitroxide radical concentration using the double signal integration method.

Figure 2:
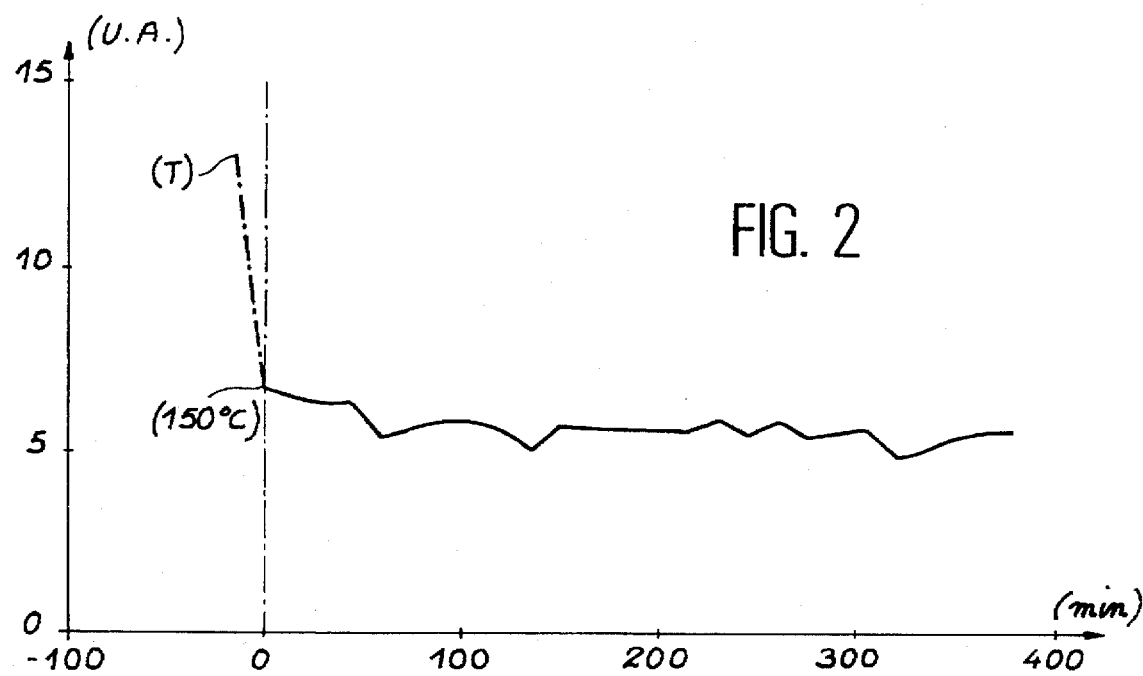
FIG. 2 A curve illustrating the stability of a nitroxide radical solution according to the invention, as a function of time (in min).

The results obtained are given in FIG. 2, which illustrates the evolution of this nitroxide radical concentration (in arbitrary units) as a function of time (in minutes).

In FIG. 2 the first point which is positioned prior to time 0 corresponds to the spectrum determined at ambient temperature. The other points starting from time 0 correspond to a temperature of 150° C.

In FIG. 2 it is possible to see a reduction of the signal during a temperature rise from ambient temperature to 150° C., but the signal then remains stable in time. At the end of the operation when the solution is returned to ambient temperature and its signal is determined a few hours later, that the latter has increased by approximately 15%. Thus, the presence of acetic acid, which serves as the oxidizing agent, makes it possible to stabilize the signal of the nitroxide radical, even for a long time at a temperature of 150° C.

FIG. 3 is a diagrammatic section of a probe of a nuclear magnetic resonance magnetometer, in which it is possible to use the solution of the invention. The probe is constituted by two similar assemblies 3 and 5 aligned along the axis Z,Z'. Each assembly comprises a coil 7 or 7' surrounding a first sample 8 or a second sample 8'. The samples are contained in two independent containers 10 and 10', constituted by symmetrical, spherical bottles, whose walls are coated with silver paint according to sectors 9 and 9' separated from one another by interruptions 11 and 11'. The exciting resonant cavity comprises two silver-coated cylinders 12 and 12' connected to the initial conductor of a coaxial cable 13.

In this uniaxial probe, the coils 7 and 7' are wound in opposite directions in such a way that the interference signals induced there are mutually compensated. However, the useful signals resulting from the electromotive forces created by the nuclear resonance phenomena are summated.

However, the above result is only obtained if the macroscopic resultant of the magnetic moments of the nuclei of the first sample 8 is opposed to the macroscopic resultant of the magnetic moments of the nuclei of the second sample 8'. In the illustrated embodiment having two exciting sources at a very high frequency, it is necessary for these opposing effects to intervene in response to the excitation, which takes place at a different frequency for both samples.

This probe is very interesting, because it makes it possible to perform measurements of magnetic fields at temperatures as high as 180° C. without destruction of the probe.

We claim:

1. Solution containing a nitroxide radical for magnetometry by nuclear magnetic resonance, said solution comprising a nitroxide radical of formula:

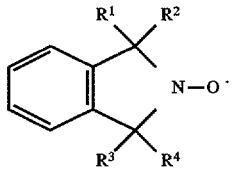

(I)

in which $R^1$, $R^2$, $R^3$ and $R^4$, which can be the same or different, represent an optionally deuterated alkyl or alkoxy group, or in which the pairs $R^1-R^2$ and/or $R^3-R^4$ together form an optionally deuterated cycloalkyl or poly-cycloalkyl group, and N represents $^{14}N$ or $^{15}N$; a solvent comprising water and from 20 to 30 volume percent ethylene glycol; and an oxidizing agent of the reduced form of the nitroxide radical.

2. Solution according to claim 1, characterized in that $R^1$, $R^2$, $R^3$ and $R^4$ represent the optionally deuterated methyl group.

3. Solution according to claim 1, characterized in that N represents $^{15}N$.

4. Solution according to claim 1, characterized in that the oxidizing agent is chosen from among metaperiodates of alkali metals and lead dioxide.

5. Solution according to claim 1, characterized in that the oxidizing agent is sodium metaperiodate.

6. Solution according to claim 1, characterized in that it contains $10^{-2}$ to $5.10^{-2}$ mole/l of oxidizing agent.

7. Solution according to claim 1, characterized in that it contains $10^{-3}$ to $10^{-2}$ mole/l of nitroxide radical.

8. Nuclear magnetic resonance magnetometer probe without forbidden axis having two assemblies, each constituted by a coil surrounding a container filled with a sample constituted by a solution containing a nitroxide radical, and two resonant cavities for exciting the two samples to two different frequencies, characterized in that the two samples are a solution of a nitroxide radical according to claim 1.

9. Solution containing a nitroxide radical for magnetometry by nuclear magnetic resonance, said solution comprising a nitroxide radical of formula:

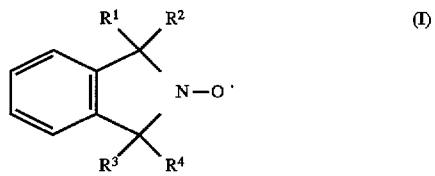

(I)

in which $R^1$, $R^2$, $R^3$ and $R^4$, which can be the same or different, represent an optionally deuterated alkyl or alkoxy group, or in which the pairs $R^1-R^2$ and/or $R^3-R^4$ together form an optionally deuterated cycloalkyl or poly-cycloalkyl group, and N represents $^{14}N$ or $^{15}N$; and a solvent comprising water and from 20 to 50 volume percent acetic acid.

10. Solution according to claim 9, characterized in that it is constituted by 1,1,3,3-tetramethylisoindolin-2-yloxyl dissolved at a concentration of $10^{-3}$ mole/l in a mixture of water and acetic acid containing 50 vol. % acetic acid.

11. Solution according to claim 9, characterized in that it contains $10^{-3}$ to $10^{-2}$ mole/l of nitroxide radical.

* * * * *